US 6,636,582 B2

(12) United States Patent
Rader et al.

(10) Patent No.: US 6,636,582 B2
(45) Date of Patent: Oct. 21, 2003

(54) MULTIPLE ENERGY X-RAY IMAGING TECHNIQUES

(75) Inventors: Amber E. Rader, New Berlin, WI (US); Mohamed Ali Hamadah, Waukesha, WI (US); Didier A. Verot, Guyancourt (FR); John J. Zhang, Waukesha, WI (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 0 days.

(21) Appl. No.: 09/683,021

(22) Filed: Nov. 8, 2001

(65) Prior Publication Data

US 2003/0086531 A1 May 8, 2003

(51) Int. Cl.[7] .................................................. H05G 1/64
(52) U.S. Cl. ................ 378/98.9; 378/98.11; 378/98.12
(58) Field of Search .......................... 378/98.9, 98.11, 378/5, 19, 62, 207, 98.12, 101, 113, 114; 250/370.11, 370.09

(56) References Cited

U.S. PATENT DOCUMENTS 5,020,085 A * 5/1991 Kawara et al. ............ 378/98.11
6,285,740 B1 * 9/2001 Seely et al. ................. 378/98.9
6,408,050 B1 * 6/2002 Han et al. ................... 378/98.9
6,501,819 B2 * 12/2002 Unger et al. .................... 378/5

* cited by examiner

Primary Examiner—Drew A. Dunn
Assistant Examiner—Courtney Thomas
(74) Attorney, Agent, or Firm—Peter J. Vogel

(57) ABSTRACT

An x-ray imaging system (10) for generating multiple energy x-ray images is provided. The system (10) includes an exposure switch (32) having an "ON"state. A console (14) is electrically coupled to the exposure switch (32) and contains two or more selected imaging program sets. An x-ray generator (18) generates x-rays. An image detector (28) detects the x-rays and generates two or more electronic signals. An image generation controller (20) is electrically coupled to the image detector (28) and controls the sequencing of the two or more electronic signals. An x-ray controller (12) is electrically coupled to the console (14) and the x-ray generator (18). The x-ray controller signals the image generation controller (20) to generate the two or more electronic signals sequentially when the exposure switch (30) is in the ON state and in response to the two or more selected imaging program sets. A method for performing the same is also provided.

22 Claims, 4 Drawing Sheets

MULTIPLE ENERGY X-RAY IMAGING TECHNIQUES

BACKGROUND OF INVENTION

The present invention relates generally to x-ray systems, and more particularly to an apparatus and method for generating multiple energy x-ray images.

X-ray systems are used for various purposes. One such purpose is to generate dual energy images of a portion of a patient. Dual energy images refer to two images consisting of separate types of tissue, an example being bone tissue and soft tissue. Dual energy images can enable a physician to better detect injuries such as broken bones or illnesses such as cancer.

Dual energy imaging involves acquiring two x-ray images by generating two exposures at different energy levels. The two images are acquired sequentially through use of an x-ray detector. The two images can be subtracted to create the tissue image and the bone image.

During image acquisition, the image quality of the subtracted images can decline due to patient movement or simply from heart and lung movement between the two exposures. Currently the primary hardware limitation is the amount of time required between when the first exposure is read to when a second exposure of different technique can be generated, which is approximately six seconds. During the six-second delay between the exposures, patient movement becomes highly probable effecting image results. Therefore, the quicker the images are acquired in time the better the image quality.

Therefore, it would be desirable to provide an improved apparatus and method for generating dual energy x-ray images so as to minimize artifacts in the soft tissue and bone images.

SUMMARY OF INVENTION

The foregoing and other advantages are provided by an apparatus and method for generating multiple energy x-ray images. An x-ray imaging system for generating two or more energy x-ray images is provided. The system includes an exposure switch having an "ON" state. A console is electrically coupled to the exposure switch and contains two or more selected imaging program sets. An x-ray generator generates x-rays. An image detector detects the x-rays and generates two or more electronic signals. An image generation controller is electrically coupled to the image detector and controls the sequencing of the two or more electronic signals. An x-ray controller is electrically coupled to the console and the x-ray generator. The x-ray controller signals the image generation controller to generate the two or more electronic signals sequentially when the exposure switch is in the ON state and in response to the two selected imaging program sets. A method for performing the same is also provided.

One of several advantages of the present invention is that it provides a two or more energy imaging system that allows for two or more imaging program sets to be selected for x-ray exposures before acquiring the first x-ray image, thereby, eliminating user interaction between a first exposure and future exposures and providing improved image quality.

Another advantage of the present invention is that it also provides parallel processing of image data, therefore, providing quicker response time from when the first exposure is taken to when two or more energy images are created and displayed.

The present invention itself, together with attendant advantages, will be best understood by reference to the following detailed description, taken in conjunction with the accompanying figures.

BRIEF DESCRIPTION OF DRAWINGS

For a more complete understanding of this invention reference should now be had to the embodiments illustrated in greater detail in the accompanying figures and described below by way of examples of the invention wherein.

DETAILED DESCRIPTION

Figure 1:
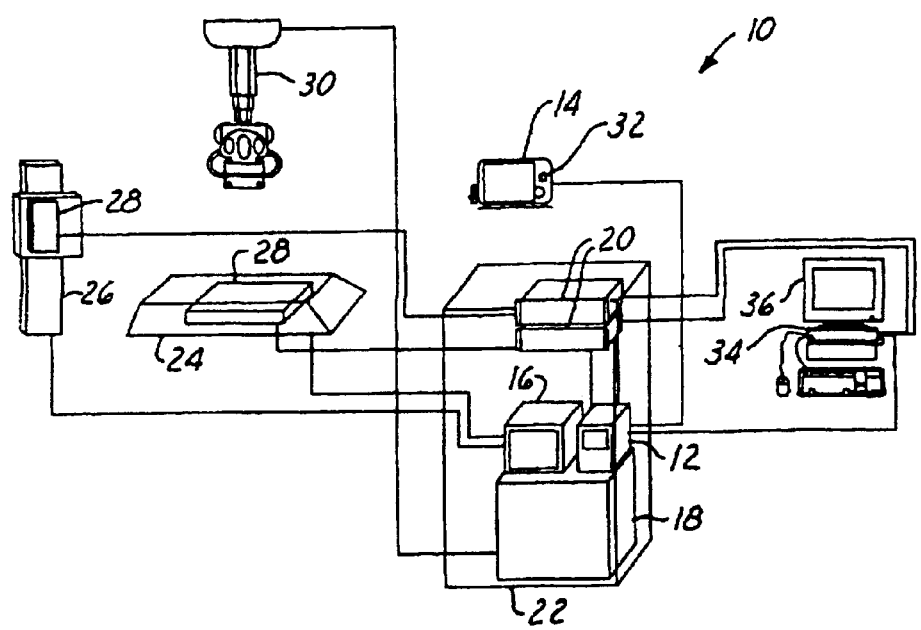
FIG. 1 is a pictorial view of an x-ray system for generating dual energy x-ray images in accordance with an embodiment of the present invention.

In each of the following figures, the same reference numerals are used to refer to the same components. While the present invention is described with respect to an apparatus and method for generating dual energy x-ray images, the present invention may be adapted to be used in various systems including: computed tomography (CT) systems, radiotherapy systems, X-ray imaging systems, and other imaging systems that can generate images at different energies.

In the following description, various operating parameters and components are described for one constructed embodiment. These specific parameters and components are included as examples and are not meant to be limiting.

Also, in the following description an x-ray subsystem may be any of the following: an x-ray controller, an image generation controller, an image detector, an x-ray generator, a computer, a console, a positioner, or various other x-ray subsystems and components.

Additionally, in the following description dual energy imaging is described to illustrate an embodiment of the present invention. The present invention may also be applied to generate more than two separate tissue images in response to multiple energy x-ray images from multiple program sets. Each x-ray image of the multiple energy x-ray images may be of the same or different energy level. For example, when three x-ray images are generated two x-ray images may be of the same energy level and the third x-ray image may be of a different energy level.

Referring now to FIG. 1, a pictorial view of an x-ray system 10 for generating dual energy x-ray images in accordance with an embodiment of the present invention is shown. The system 10 includes an x-ray system controller 12 electrically coupled to a console 14, a patient positioner 16, an x-ray generator 18, and image generation controllers 20. The x-ray system controller 12, the positioner 16, the x-ray generator 18, and the image generation controllers 20 are contained within cabinet 22. The x-ray system controller 12 controls the positioner, x-ray generation, and initialization of x-ray subsystems in response to dual program sets manually selected on the console 14. The dual program sets contain two x-ray imaging techniques. The positioner 16 is electrically coupled to a table 24 and a wallstand 26, both of which have a detector 28 and a corresponding image generation controller 20. The image generation controllers 20 are electrically coupled to an x-ray tube 30. The x-ray system controller 12 signals the image generation controllers 20 to generate dual electronic signals sequentially when an exposure switch 32 is in an "ON" state and in response to the dually selected imaging program sets. The two images contained within the dual electronic signals are corrected by the image generation controllers 20 transmitted to an acquisition and visualization workstation 34, which is electrically coupled to the x-ray controller 12 and the image generation controllers 20. The workstation 34 converts the corrected electronic signals into visual dual energy images that are viewed on a monitor 36. The x-ray tube 30, the table 24, the wallstand 26, the positioner 16, and the x-ray generator 18 are known components in the art.

The console 14 although similar to consoles known in the art allows for selection of two program sets. Each program set contains parameters associated with generating a high energy level exposure and a low-energy level exposure. The parameters may include: patient size, x-ray generation energy levels, x-ray generation speeds, sequencing of x-ray generation, or other various parameters associated with generating dual energy images.

The x-ray controller 12 as well as the image generation controllers 20 and the workstation 34, are preferably microprocessor based such as a computer having a central processing unit, memory (RAM and/or ROM), and associated input and output buses. The x-ray controller 12, the image generation controllers 20, and the workstation 34 may be a portion of a central main control unit, an electronic control module, or may each be a stand-alone controller or a workstation.

The x-ray controller 12 performs various tasks including generating dual x-ray information signals in response to the dually selected imaging program sets. The information signals contain information related to and may include the dually selected program sets, which are used by the workstation 34 in generating the dual energy images. Other x-ray controller 12 tasks will become more evident below.

Figure 2:
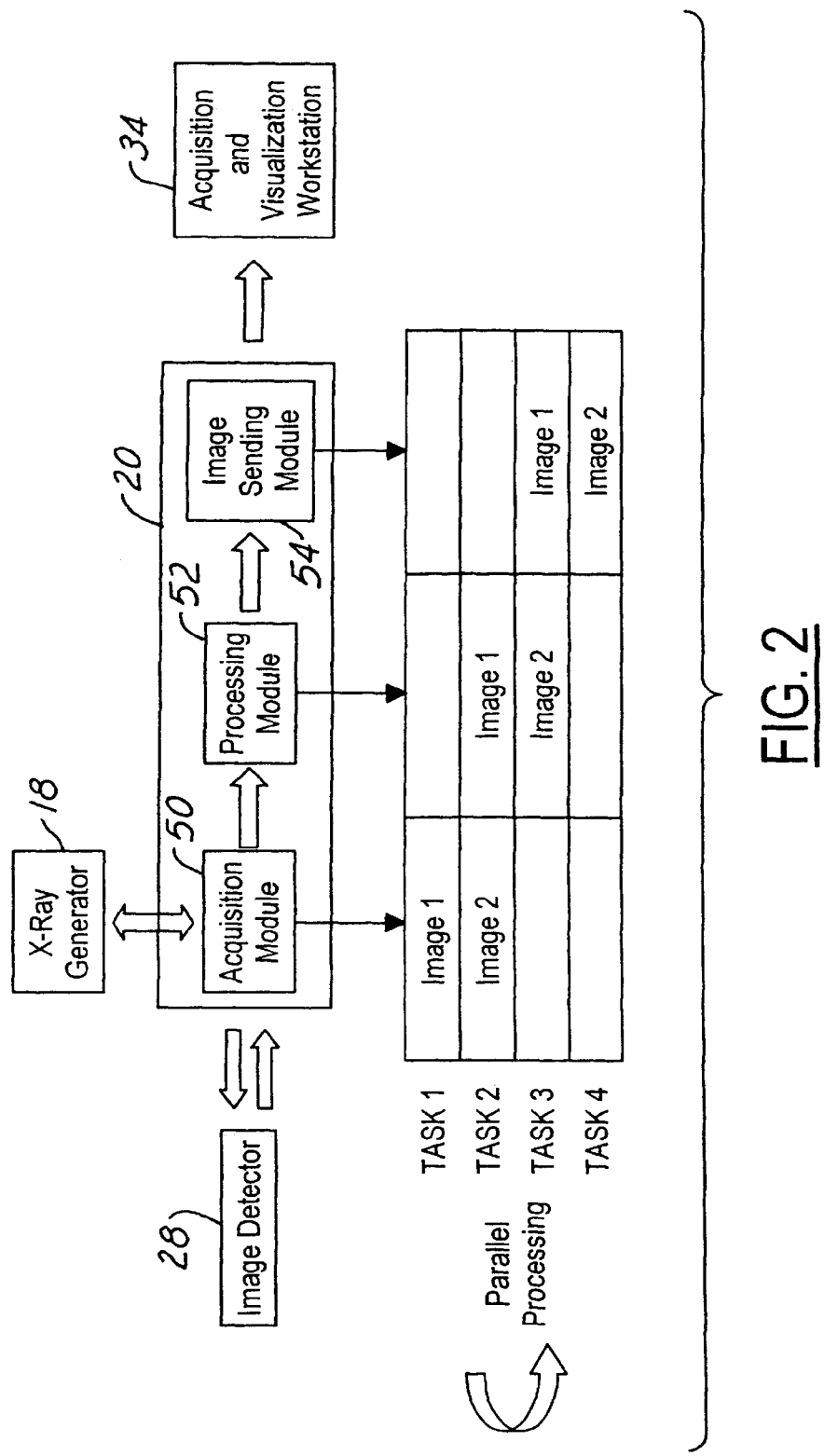
FIG. 2 is a block diagrammatic view and parallel processing of an image generation controller and associated inputs and outputs in accordance with an embodiment of the present invention.

Referring now to FIG. 2, a block diagrammatic view and parallel processing of the image generation controllers 20 and associated inputs and outputs in accordance with an embodiment of the present invention is shown. The image generation controllers 20 contain three modules: an acquisition module 50, a processing module 52, and an image sending module 54, which are software based. The image-sending module 54 transmits the correct dual x-ray images to the workstation 34.

The acquisition module 50 signals the detector 28 to generate the dual electronic signals, which are then received sequentially by the acquisition module 50. The acquisition module 50 also controls the synchronization of the x-ray generator 18 with the acquisition of the dual electronic signals from the detector 28.

The processing module 52 processes the dual x-ray images. The processing module 52 contains corrections associated with the various system irregularities. The corrections may include maps for determining where bad pixels exist, where nonconformities exist, where rotational issues exist, or other corrections known in the art that may need to be performed.

The image generation controller 20 performs the tasks of the acquisition module 50, the processing module 52, and the image-sending module 54 in a parallel format. As illustrated by tasks 1–4 in FIG. 2. For example, in task 2 the first image is being processed as the second image is being acquired. In task 3 the first image is being transmitted to the workstation 34 as the second image is being processed.

Figure 3:
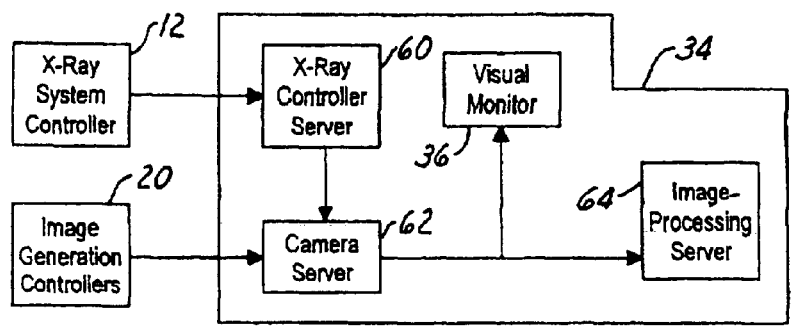
FIG. 3 is a block diagrammatic view of an acquisition and visualization workstation and associated inputs in accordance with an embodiment of the present invention.

Referring now to FIG. 3, a block diagrammatic view of the workstation 34 and associated inputs in accordance with an embodiment of the present invention is shown. The workstation 34 contains three servers: an x-ray controller server 60, a camera server 62, and an image processing server 64, which are also software based.

The x-ray controller server 60 stores the dual x-ray information signals received from the x-ray controller 12. The information signals contain techniques used in generating the high-energy exposure and the low-energy exposure.

The camera server 62 receives the dual corrected electronic signals from one of the image generation controllers 20 in a dual acquisition sequence and converts the dual corrected electronic signals into dual energy x-ray images. The dual energy x-ray images may be viewed on monitor 36. The camera server 62 handles acquisition sequencing for reception of the corrected dual electronic signals from the image generation controllers 20. The camera server 62 also formats the dual energy images such that they are compliant with the Digital of Imaging and COmmunication in Medicine (DICOM) standard.

The image-processing server 64 performs execution of an image-processing task. The image-processing task refers to the subtraction of the dual energy images to separate the desired tissues.

Figure 4:
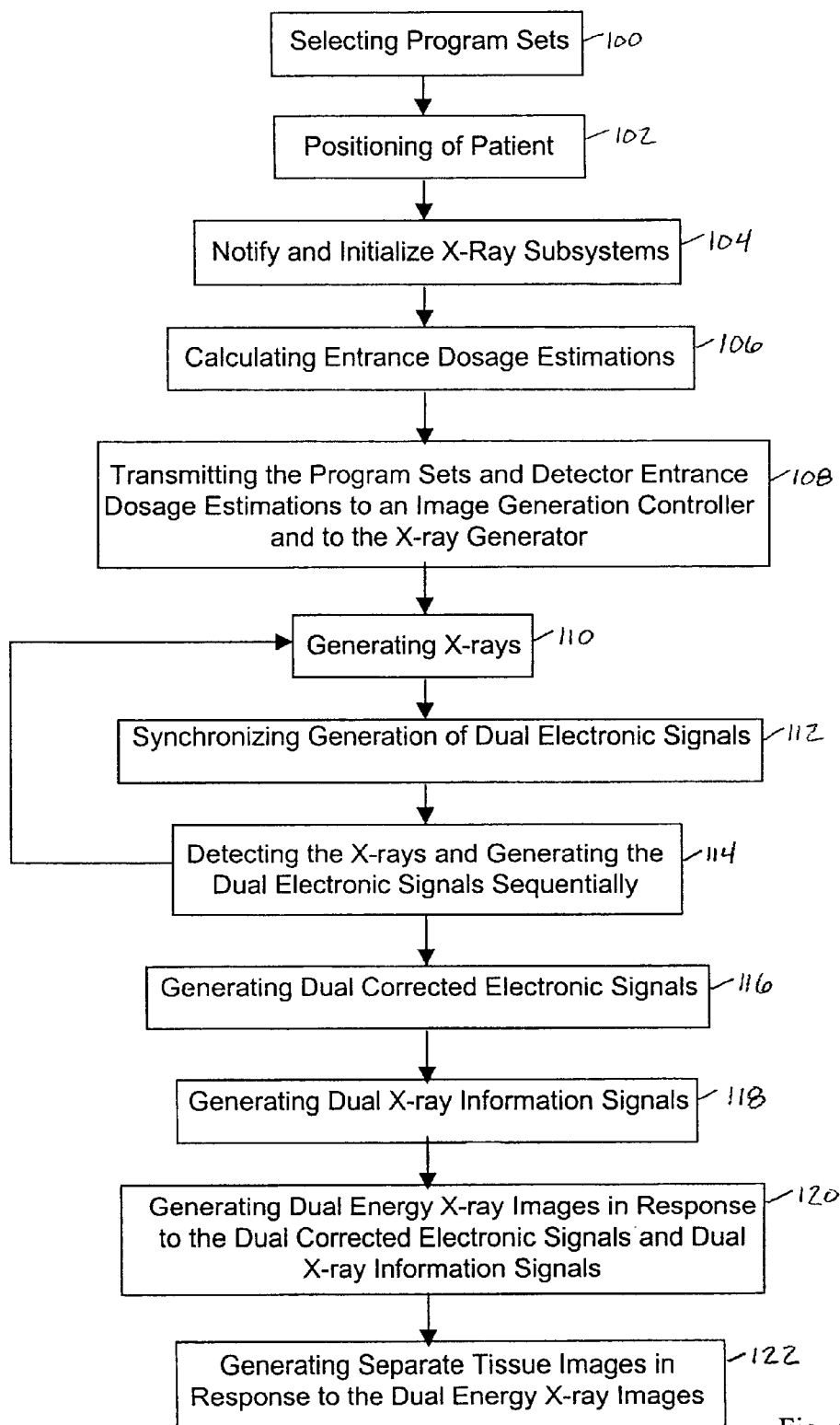
FIG. 4 is a logic flow diagram illustrating a method of generating dual energy x-ray images in accordance with an embodiment of the present invention.

Referring now to FIG. 4, a logic flow diagram illustrating a method of generating dual energy x-ray images in accordance with an embodiment of the present invention is shown.

In step 100, the operator creates, enables, selects, edits, and saves two x-ray techniques for dual energy exposures into dedicated dual energy protocol procedures such as the program sets above mentioned. In other words a first Xray technique set and a second Xray technique set are selected for the high-energy exposure and the low-energy exposure, respectively.

In step 102, a patient is oriented on the table 24 or in front of the wallstand 26. The table 24 or the wallstand 26 is appropriately positioned with respect to the tube 30 via the positioner 16.

In step 104, when the exposure switch 32 is in the "ON"position and after selection of the dual energy program sets, the x-ray system controller 12 coordinates and notifies x-ray subsystems including the x-ray generator 18, the positioner 16, the image generation controllers 20, and the workstation 14 to setup, configure, and prepare the system 10 for dual energy x-ray exposures. This action serves to confirm readiness for the x-ray exposure as well as send the number of x-ray exposures and the program set for a first dual energy x-ray exposure to the x-ray generator 18.

In step 106, the x-ray system controller 12 calculates detector entrance dosage estimations, which are later used by the image generation controller 20.

In step 108, the x-ray controller transmits the program set for the first exposure and the detector entrance dosage estimations to the image generation controller 20 and the x-ray generator 18 when the exposure switch 32 is in the "ON" position. The x-ray controller also transmits the program set for the first exposure as well as the number of exposures to the x-ray generator.

In step 110, the x-ray system controller 12 signals the x-ray generator and the image generation controller to begin the x-ray sequence. In so doing, the x-ray subsystems are configured for the first exposure, followed by generating x-rays for the first exposure. The x-ray subsystems are then reconfigured for the second exposure, followed by generating x-rays for the second exposure after performing steps 112 and 114.

In step 112, the image generation controller 20 synchronizes generation of the dual electronic signals. Steps 110 and 112 may be performed simultaneously.

In step 114, the appropriate detector 28 detects x-rays generated by the x-ray generator 18 passing through the patient, from the tube 30 to the detector 28, and generates the dual electronic signals sequentially. The x-ray generator 18 performs a first x-ray exposure, corresponding to the first x-ray technique, to generate a first x-ray image. The x-ray system controller 12 is then signaled that the first exposure is completed. Upon completion of the first exposure, the image generation controller 20 receives the first x-ray image from the detector 28. While the exposure switch 32 is still in the "On" position, the x-ray generator 18 performs a second x-ray exposure method, corresponding to the second imaging program set, upon completion of said first x-ray signal and reconfiguring of said x-ray subsystems for the second exposure.

Steps 110 through 114 are performed for a first x-ray signal and then repeated for a second x-ray signal of the dual electronic signals.

In step 116, the image generation controller generates dual corrected x-ray images in response to the dual electronic signals as described above.

In step 118, the x-ray system controller 12 generates dual x-ray information signals in response to the first imaging parameter set and the second imaging parameter set. The information contained within the x-ray information signals is placed into a DICOM header when the dual x-ray images are generated on the Acquisition and Visualization workstation.

In step 120, the workstation 34 stores the dual x-ray information signals. Workstation 34 receives the dual corrected electronic signals in a dual acquisition sequence, corresponding to the first imaging program set and the second imaging program set. The workstation 34 generates dual energy x-ray images in response to the dual corrected electronic signals and the dual x-ray information signals by using similar methods known in the art for generating a single x-ray image.

In step 122, the workstation 34 then generates separate tissue images in response to the dual energy x-ray images as described above.

The present invention by providing an x-ray system that allows for selection of two program sets before generation of dual x-ray images provides a shorter delay time between a first exposure and a second exposure and no user interaction between. The present invention also provides decreased total processing time in generating, processing, and recording of dual x-ray images. Thereby, providing a system that generates dual energy x-ray images having increased quality over systems requiring user interaction to acquire two images of different technique.

The above-described apparatus, to one skilled in the art, is capable of being adapted for various purposes and is not limited to the following systems: CT systems, radiotherapy systems, X-ray imaging systems, and other imaging systems that can generate dual energy images. The above-described invention may also be varied without deviating from the spirit and scope of the invention as contemplated by the following claims.

What is claimed is:

1. An x-ray imaging system for generating multiple energy x-ray images comprising:

an exposure switch comprising an "ON" state;

a console electrically coupled to said exposure switch comprising two or more selected imaging program sets;

an x-ray generator configured to generate x-rays;

an image detector configured to detect said x-rays and generate two or more electronic signals;

an image generation controller electrically coupled to said image detector and configured to parallely and simultaneously control sequencing of said two or more electronic signals; and an x-ray controller electrically coupled to said console, said x-ray generator, and said image generation controller, said x-ray controller configured to signal said image generation controller to generate said two or more electronic signals sequentially when said exposure switch is in said ON state and in response to said two or more selected imaging program sets.

2. A system as in claim 1 wherein said image generation controller configured to generate two or more corrected electronic signals in response to said two or more electronic signals.

3. A system as in claim 2 wherein the image generation controller comprises:

an acquisition module configured to receive said two or more electronic signals;

a processing module configured to convert said two or more electronic signals into said two or more corrected electronic signals; and an image sending module configured to transmit said two or more corrected electronic signals to an acquisition and visualization workstation.

4. A system as in claim 3 wherein said image generation controller is a parallel processor.

5. A system as in claim 2 further comprising:

said x-ray controller configured to generate two or more x-ray information signals in response to said two or more selected imaging program sets;

an acquisition and visualization workstation configured to generate two or more energy x-ray images in response to said two or more corrected electronic signals and said two or more x-ray information signals.

6. A system as in claim 5 wherein said acquisition and visualization workstation comprises:

an x-ray controller server configured to store said two or more selected imaging program sets; and a camera server configured to receive said two or more corrected electronic signals in a two or more acquisition sequence and converting said two or more corrected electronic signals into x-ray images.

7. A system as in claim 6 wherein said two or more x-ray images are compliant with digital imaging and communication in medicine standard.

8. A system as in claim 6 further comprising an image processing server configured to subtract said two or more corrected electronic signals to generate a soft tissue image and a bone image.

9. A system as in claim 1 wherein said two or more selected imaging program sets comprise two or more energy parameters corresponding to said two or more electronic signals.

10. A method of generating two or more energy x-ray images comprising:

selecting a plurality of imaging program sets then;

generating x-rays;

synchronizing the generation of two or more electronic signals;

detecting said x-rays and generating said two or more electronic signals; and generating said two or more electronic signals sequentially and in response to said plurality of imaging program sets.

11. A method as in claim 10 wherein generating two or more electronic signals comprises:

performing a first x-ray exposure method, corresponding to a first program set of said plurality of program sets, to generate a first electronic signal;

signaling said x-ray system controller that said first exposure is completed;

receiving a first electronic signal; and performing a second x-ray exposure method, corresponding to a second imaging program set of said plurality of program sets, upon completion of receiving said first electronic signal and reconfiguring of said x-ray subsystems for said second exposure.

12. A method as in claim 10 further comprising generating two or more corrected electronic signals in response to said two or more electronic signals.

13. A method as in claim 10 further comprising:

generating two or more x-ray information signals in response to said first imaging program set and said second imaging program set; and generating two or more energy x-ray images in response to said two or more corrected electronic signals and said two or more x-ray information signals.

14. A method as in claim 13 further comprising:

storing said two or more x-ray information signals;

receiving said two or more corrected electronic signals in two or more acquisition sequences, corresponding to said plurality of imaging program sets; and converting said two or more corrected electronic signals into two or more x-ray images.

15. A method as in claim 13 further comprising subtracting said two or more corrected electronic signals to form a soft tissue image and a bone image.

16. A method as in claim 10 further comprising:

notifying an x-ray subsystem that a two or more energy procedure is selected; and initializing said x-ray subsystems in response to said notification.

17. A method as in claim 10 further comprising:

calculating an x-ray detector entrance dosage; and generating two or more corrected electronic signals in response to said x-ray detector entrance dosage.

18. A method as in claim 10 wherein generating x-rays comprises:

configuring x-ray subsystems for a first exposure;

generating x-rays for said first exposure;

reconfiguring said x-ray subsystems for a second exposure; and generating x-rays for said second exposure.

19. A method of generating two or more energy x-ray images comprising:

selecting a plurality of imaging program sets than;

acquiring a first x-ray image in response to a first imaging program set of said plurality of program sets; and then processing said first x-ray image while acquiring a second x-ray image in response to a second imaging program set of said plurality of program sets.

20. A method as in claim 19 further comprising processing said second x-ray image while sending said first x-ray image.

21. An x-ray imaging system for generating two or more energy x-ray images comprising:

an exposure switch comprising an "ON" state;

a console electrically coupled to said exposure switch comprising two or more selected imaging program sets;

an x-ray generator configured to generate x-rays;

an image detector configured to detect said x-rays and generate two or more electronic signals;

an image generation controller electrically coupled to said image detector and configured to parallely and simultaneously control the sequencing of said two or more electronic signals and generating two or more corrected electronic signals in response to said two or more electronic signals;

an x-ray controller electrically coupled to said console, said x-ray generator, and said image generation controller, said x-ray controller configured to signal said image generation controller to generate said two or more electronic signals sequentially when said exposure switch is in said ON state and in response to said two or more selected imaging program sets; and wherein said x-ray controller configured to generate two or more x-ray information signals in response to said two or more selected imaging program sets; and an acquisition and visualization workstation configured to generate two or more energy x-ray images in response to said two or more corrected electronic signals and said two or more x-ray information signals.

22. A system as in claim 21 wherein the image generation controller comprises:

an acquisition module configured to receive said two or more electronic signals;

a processing module configured to convert said two or more electronic signals into said two or more corrected electronic signals; and an image sending module configured to transmit said two or more corrected electronic signals to said acquisition and visualization workstation.

* * * * *